United States Patent [19]

Gerken et al.

[11] Patent Number: 5,602,108

[45] Date of Patent: Feb. 11, 1997

[54] SEMISYNTHETIC DIASTEREOMERICALLY PURE N-GLYCIDYLANTHRACYCLINES, A PROCESS FOR THE STEREOSELECTIVE PREPARATION THEREOF AS THE USE THEREOF AS CYTOSTATICS

[75] Inventors: Manfred Gerken, Marburg; Monika Grimm, Biebertal; Ernst Raab, Marburg; Dieter Hoffmann, Marburg; Reiner Straub, Marburg, all of Germany

[73] Assignee: Behringwerke Aktiengesellschaft, Marburg, Germany

[21] Appl. No.: 464,468

[22] Filed: Jun. 5, 1995

Related U.S. Application Data

[63] Continuation of Ser. No. 358,676, Dec. 19, 1994, abandoned, which is a continuation of Ser. No. 198,378, Feb. 18, 1994, abandoned, which is a continuation of Ser. No. 71,347, Jun. 3, 1993, abandoned, which is a continuation of Ser. No. 789,986, Nov. 12, 1991, abandoned.

[30] Foreign Application Priority Data

Nov. 14, 1990 [DE] Germany ............... 40 36 155.1

[51] Int. Cl.⁶ ............... A61K 37/00; C07M 15/24
[52] U.S. Cl. ............... 514/34; 536/6.4
[58] Field of Search ............... 536/6.4; 574/34

[56] References Cited

U.S. PATENT DOCUMENTS

| | | |
|---|---|---|
| 4,408,063 | 10/1983 | Baldwin et al. |
| 4,877,870 | 10/1989 | Umezawa et al. ............... 536/6.4 |
| 4,948,880 | 8/1990 | Hermentin et al. ............... 536/6.4 |

OTHER PUBLICATIONS

J. J. Baldwin, A. W. Raab, K Mensler, B. H. Arison, and D. E. McClure, Synthesis of (R)- and (S)-Epichlorohydrin, J. Orig. Chem, vol. 43, Jun. 30, 1978, pp. 4876-4878.

Yuhsuke Kawakami, Tamio Asai, Kiyoshi Umeyama, and Yuya Yamashita Selectively Deuterated and Optically Active Cyclic Ethers, J. Orig. Chem, vol. 47, Jun. 1, 1981, pp. 3581-3585.

Janice M. Klunder, Soo Y. Ko, and K. Barry Sharpless, Asymmetric Epoxidation of Allyl Alcohol: Efficient Routes to Homochiral β-Adrenergic Blocking Agents, J. Orig. Chem, vol. 51, Apr. 15, 1986, pp. 3710-3712.

R. E. Parker and N. S. Isaacs, Mechanisms Of Epoxide Reactions, Chem Rev. 59, Apr. 17, 1959, pp. 737, 799.

*Primary Examiner*—Elli Peselev
*Attorney, Agent, or Firm*—Finnegan, Henderson, Farabow, Garrett & Dunner, L.L.P.

[57] ABSTRACT

Semisynthetic diastereomerically pure N-glycidylanthracyclines, a process for the stereoselective preparation thereof and the use thereof as cytostatics. The invention relates to anthracyclines having cytostatic activity and the formula I, which are, where appropriate, in the form of a salt with an inorganic or organic acid,

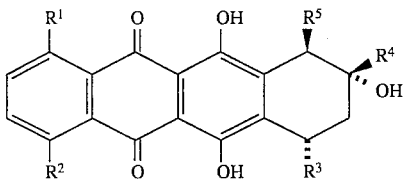

in which $R^1$ is hydrogen or a hydroxyl group, $R^2$ is hydrogen, a hydroxyl group or an alkyloxy group ($C_1$–$C_4$), $R^3$ is hydrogen, a hydroxyl group or a structure of the formula II

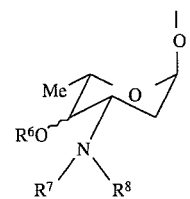

$R^4$ is $CH_2CH_3$, $COCH_3$, $COCH_2OH$, $CHOHCH_3$ or $CHOHCH_2OH$, $R^5$ is hydrogen, a hydroxyl group, a methoxycarbonyl group or a structure of the formula II, $R^6$ is hydrogen, an alkyl group ($C_1$–$C_4$), an allyl group, a benzyl group or mono- or di-methyloxy-substituted benzyl group, a tetrahydropyranyl group, $R^7$ is hydrogen, an alkyl group ($C_1$–$C_4$), an allyl group, a benzyl group or mono- or di-methyloxy-substituted benzyl group and $R^8$ is a structure of the formula III or IV

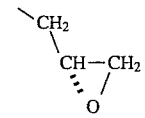

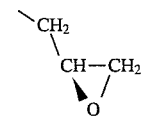

and to a process for the preparation of these compounds, which comprises reacting an anthracycline derivative of the structure I in which $R^1$, $R^2$ and $R^4$ are as defined above, and $R^3$ is hydrogen, a hydroxyl group or a structure of the formula V

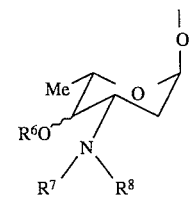

$R^5$ is hydrogen, a hydroxyl group, a methoxycarbonyl group or a structure of the formula V and $R^6$ and $R^7$ are as defined above, with (R)- or (S)-glycidyl sulfonate.

9 Claims, No Drawings

SEMISYNTHETIC DIASTEREOMERICALLY PURE N-GLYCIDYLANTHRACYCLINES, A PROCESS FOR THE STEREOSELECTIVE PREPARATION THEREOF AS THE USE THEREOF AS CYTOSTATICS

This application is a continuation, of application Ser. No. 08/358,676, filed Dec. 19, 1994, abandoned, which was a continuation of Ser. No. 08/198,378, filed Feb. 18, 1994, abandoned, which was a continuation of application Ser. No. 08/071,347, filed Jun. 3, 1993 abandoned, which was a continuation of application Ser. No. 07/789,986, filed Nov. 12, 1991, abandoned.

The present invention relates to N-(R)-glycidylanthracyclines and N-(S)-glycidylanthracyclines having cytostatic activity and the formula I

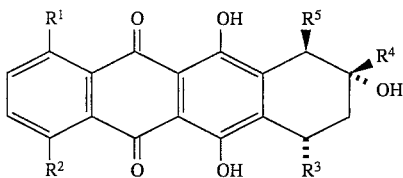

in which $R^1$ is hydrogen or a hydroxyl group, $R^2$ is hydrogen, a hydroxyl group or an alkyloxy group ($C_1$–$C_4$), $R^3$ is hydrogen, a hydroxyl group or a structure of the formula II

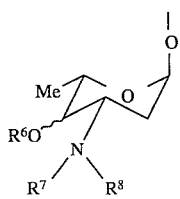

$R^4$ is $CH_2CH_3$, $COCH_2OH$, $CHOHCH_3$ or $CHOHCH_2OH$, $R^5$ is hydrogen, a hydroxyl group, a methoxycarbonyl group or a structure of the formula II, where either $R^3$ or $R^5$ or both must be a structure of the formula II, $R^6$ is hydrogen, an alkyl group ($C_1$–$C_4$), an allyl group, a benzyl group or mono- or di-methyloxy-substituted benzyl group, a tetrahydropyranyl group, $R^7$ is hydrogen, an alkyl group ($C_1$–$C_4$), an allyl group, a benzyl group or mono- or di-methyloxy-substituted benzyl group and $R^8$ is a structure of the formula III or IV

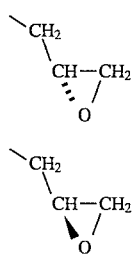

and to a process for the stereoselective preparation of diastereomerically pure N-glycidylanthracycline derivatives, especially of 7-O-(3-N-methyl-3-N-(R)-glycidyl-α-L-daunosaminyl)-β-rhodomycinone and 7-O-(3-N-methyl-3-N-(S)-glycidyl-α-L-daunosaminyl)-β-rhodomycinone, which are suitable by reason of their cytostatic activity for the treatment of cancers.

The preparation of 7-O-(3-N-methyl-3-N-(R/S)-glycidyl-α-L-daunosaminyl)-β-rhodomycinone and its cytotoxic activity is described in the Patent Application DE 3,819,092 A1 as stereounspecific synthesis. This process starts from racemic epibromohydrin which undergoes addition onto the N-methylamino group of the daunosamine on the anthracycline. This results in compounds according to the invention as mixture of diastereomers which can be separated with heavy losses only using multiple elaborate chromatographic methods. It has emerged from this that, because of the enormous instability of the compounds, chromatography of the mixture of R/S diasteromers was unable to provide the pure diastereomers in the necessary purity and required amount because a large part of the amount of substance was irreversibly bound to the silica gel support during the separation.

U.S. Pat. No. 4,408,063, J. Org. Chem. 43, 4876–4878 (1978) and J. Org. Chem. 47, 3581–3585 (1982) disclose the preparation of R- and S-epibromohydrin, these being multistage elaborate syntheses which, on reproduction, provide only inadequate yields of R- and S-epibromohydrin of insufficient optical purity.

It has been found, completely surprisingly, that 7-O-(3-N-methyl-3-N-(S)-glycidyl-α-L-daunosaminyl)-β-rhodomycinone is obtained directly on reaction of 7-O-(3-N-methyl-α-L-daunosaminyl)-β-rhodomycinone (DE 3,641,833 A1) with an intermediate from the epibromohydrin synthesis, namely 3-bromo-1-tosyloxy-2-(R)-propanol (J. Org. Chem. 47, 3581–3585 (1982)).

It has furthermore been found, surprisingly, that (R)-glycidyl tosylate and (S)-glycidyl tosylate which can be prepared easily and very enantiomerically pure by Sharpless epoxidation and subsequent tosylation from allyl alcohol (J. Org. Chem. 51, 3710–3712 (1986)) can likewise be reacted with 7-O-(3-N-methyl-α-L-daunosaminyl)-β-rhodomycinone to give 7-O-(3-N-methyl-3-N-(S)-glycidyl-α-L-daunosaminyl)-β-rhodomycinone.

It has surprisingly been possible to purify the reaction products by chromatography on silica gel which has been pretreated with acidic aqueous buffer and inactivated, without large amounts of substance irreversibly binding to the silica gel.

Starting from this prior art, the invention is based on the object of developing a novel process which provides N-(R)-glycidylanthracyclines and N-(S)-glycidylanthracyclines in a stereoselective synthesis in good yields and in a purity above 96% and which is a simplification compared with known processes.

This object is achieved according to the invention by the process for the preparation of N-(R)-glycidylanthracyclines or N-(S)-glycidylanthracyclines of the formula I

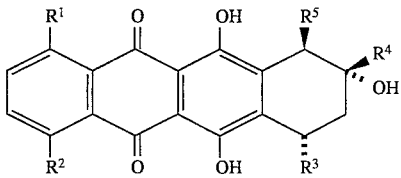

in which $R^1$ is hydrogen or a hydroxyl group, $R^2$ is hydrogen, a hydroxyl group or an alkyloxy group ($C_1$–$C_4$), $R^3$ is hydrogen, a hydroxyl group or a structure of the formula II

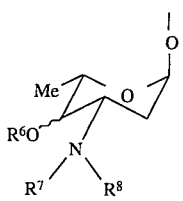

II

R⁴ is CH₂CH₃, COCH₃, COCH₂OH, CHOHCH₃ or CHOHCH₂OH,

R⁵ is hydrogen, a hydroxyl group, a methoxycarbonyl group or a structure of the formula II, where either R³ or R⁵ or both must be a structure of the formula II, R⁶ is hydrogen, an alkyl group (C₁–C₄), an allyl group, a benzyl group or mono- or di-methyloxy-substituted benzyl group, a tetrahydropyranyl group, R⁷ is hydrogen, an alkyl group (C₁–C₄), an allyl group, a benzyl group or mono- or di-methyloxy-substituted benzyl group and R⁸ is a structure of the formula III or IV

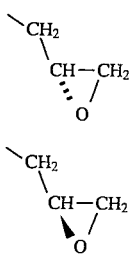

III

IV which comprises reacting an anthracycline derivative of the structure I in which R¹, R² and R⁴ are as defined above, and R³ is hydrogen, a hydroxyl group or a structure of the formula V

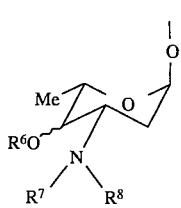

V

R⁵ is hydrogen, a hydroxyl group, a methoxycarbonyl group or a structure of the formula V, where either R³ or R⁵ or both must be a structure of the formula V, and R⁶ and R⁷ are as defined above, with an (R)- or (S)-glycidyl sulfonate, for example (R)-or (S)-glycidyl tosylate, (R)- or (S)-glycidyl mesylate, (R)- or (S)-glycidyl brosylate or (R)- or (S)-glycidyl trifluoromethane sulfonate, and isolating the product.

It is possible for this purpose to stir in the presence of a base, for example potassium carbonate, triethylamine or pyridine, and in a suitable organic solvent or solvent mixture, for example N,N-dimethylformamide or acetonitrile, at 20° C. to the reflux temperature of the solvent for 1 to 48 hours and to work up the reaction solution. It can be worked up by isolating the crude product from the solution, where appropriate after neutralization, by concentration or extraction and, where appropriate, purifying it, preferably by chromatographic separation on silica gel inactivated with an aqueous buffer solution, resulting in the product of the formula I in a purity greater than 96%.

The compounds of the formula I which are preferably prepared by the process according to the invention are those in which R¹ is a hydroxyl group, R² is a hydroxyl group or a methyloxy group, R³ is a structure of the formula II

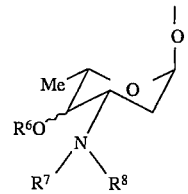

II

R⁴ is CH₂CH₃, COCH₃, COCH₂OH,

R⁵ is hydrogen, a hydroxyl group or a methoxycarbonyl group,

R⁶ is hydrogen or a tetrahydropyranyl group,

R⁷ is hydrogen or methyl,

R⁸ is a structure of the formula III or IV

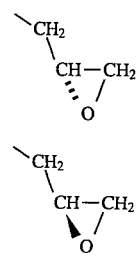

III

IV

The invention also relates to N-glycidylanthracycline derivatives which correspond to the following formula I, and to the salts thereof with an inorganic or organic acid, in which R¹ is hydrogen or a hydroxyl group, R² is hydrogen, a hydroxyl group or an alkyloxy group (C₁–C₄), R³ is hydrogen, a hydroxyl group or a structure of the formula II, R⁴ is CH₂CH₃, COCH₃, COCH₂OH, CHOHCH₃ or CHOHCH₂OH, R⁵ is hydrogen, a hydroxyl group, a methoxycarbonyl group or a structure of the formula II, where either R³ or R⁵ or both must be a structure of the formula II, R⁶ is hydrogen, an alkyl group (C₁–C₄), an allyl group, a benzyl group or mono- or di-methyloxy-substituted benzyl group, a tetrahydropyranyl group, R⁷ is hydrogen, an alkyl group (C₁–C₄), an allyl group, a benzyl group or mono- or di-methyloxy-substituted benzyl group and R⁸ is a structure of the formula III or IV.

The following are preferred:

N-glycidylanthracycline derivatives of the formula I in which

R¹ is hydrogen or a hydroxyl group,

R² is hydrogen, a hydroxyl group or a methoxy group,

R³ is a structure of the formula II,

R⁴ is CH₂CH₃, COCH₂OH, CHOHCH₃ or CHOHCH₂OH,

R⁵ is hydrogen, a hydroxyl group, a methoxycarbonyl group or a structure of the formula II, $R^6$ is hydrogen, an alkyl group ($C_1$–$C_4$), an allyl group, a benzyl group or mono- or di-methyloxy-substituted benzyl group, a tetrahydropyranyl group, $R^7$ is hydrogen, an alkyl group ($C_1$–$C_4$), an allyl group, a benzyl group or mono- or di-methyloxy-substituted benzyl group and $R^8$ is a structure of the formula III or IV;

N-glycidylanthracycline derivatives of the formula I in which $R^1$ is hydrogen or a hydroxyl group, $R^2$ is hydrogen, a hydroxyl group or a methoxy group, $R^3$ is a structure of the formula II, $R^4$ is $CH_2CH_3$, $COCH_3$, $COCH_2OH$, $CHOHCH_3$ or $CHOHCH_2OH$, $R^5$ is hydrogen, a hydroxyl group, a methoxycarbonyl group, $R^6$ is hydrogen, an alkyl group ($C_1$–$C_4$), an allyl group, a benzyl group or mono- or di-methyloxy-substituted benzyl group, a tetrahydropyranyl group, $R^7$ is hydrogen, an alkyl group ($C_1$–$C_4$), an allyl group, a benzyl group or mono- or di-methyloxy-substituted benzyl group and $R^8$ is a structure of the formula III or IV;

N-glycidylanthracycline derivatives of the formula I in which $R^1$ is hydrogen, $R^2$ is hydrogen, a hydroxyl group or a methoxy group, $R^3$ is a structure of the formula II, $R^4$ is $CH_2CH_3$, $COCH_3$, $COCH_2OH$, $CHOHCH_3$ or $CHOHCH_2OH$, $R^5$ is hydrogen, a hydroxyl group, a methoxycarbonyl group, $R^6$ is hydrogen, a tetrahydropyranyl group, $R^7$ is hydrogen, an alkyl group ($C_1$–$C_4$), an allyl group, a benzyl group or mono- or di-methyloxy-substituted benzyl group and $R^8$ is a structure of the formula III or IV;

N-glycidylanthracycline derivatives of the formula I in which $R^1$ is hydrogen, $R^2$ is hydrogen, a hydroxyl group or a methoxy group, $R^3$ is a structure of the formula II, $R^4$ is $CH_2CH_3$, $COCH_3$, $COCH_2OH$, $CHOHCH_3$ or $CHOHCH_2OH$, $R^5$ is hydrogen, a hydroxyl group, a methoxycarbonyl group, $R^6$ is hydrogen, a tetrahydropyranyl group, $R^7$ is hydrogen, an alkyl group ($C_1$–$C_4$), an allyl group and $R^8$ is a structure of the formula III or IV;

N-glycidylanthracycline derivatives of the formula I in which $R^1$ is hydrogen, $R^2$ is a hydroxyl group or a methoxy group, $R^3$ is a structure of the formula II, $R^4$ is $CH_2CH_3$, $COCH_3$ or $COCH_2OH$, $R^5$ is hydrogen, a hydroxyl group, $R^6$ is hydrogen, $R^7$ is hydrogen, an alkyl group ($C_1$–$C_4$), an allyl group and $R^8$ is a structure of the formula III or IV;

N-glycidylanthracycline derivatives of the formula I in which $R^1$ is hydrogen, $R^2$ is a hydroxyl group, $R^3$ is a structure of the formula II, $R^4$ is $CH_2CH_3$, $R^5$ is a hydroxyl group, $R^6$ is hydrogen, $R^7$ is a methyl group and $R^8$ is a structure of the formula III or IV;

N-glycidylanthracycline derivatives of the formula I in which $R^1$ is hydrogen, $R^2$ is a hydroxyl group, $R^3$ is a structure of the formula II, $R^4$ is $CH_2CH_3$, $R^5$ is a hydroxyl group, $R^6$ is hydrogen, $R^7$ is a methyl group and $R^8$ is a structure of the formula III.

The following examples explain the invention in more detail without restricting it:

Example 1:

7-O-(3-N-Methyl-3-N-(R)-glycidyl-α-L-daunosaminyl)-β-rhodomycinone

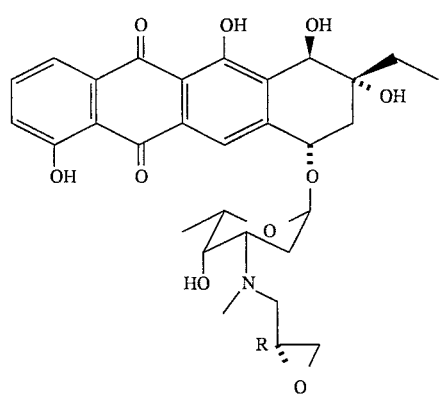

(R)-Glycidyl tosylate (2.7 g, 11.83 mmol) and potassium carbonate (3.2 g, 23.9 mmol) are added successively to a solution of 7-O-(3-N-methyl-α-L-daunosaminyl)-β-rhodomycinone (1.25 g, 2.36 mmol) in dry N,N-dimethylformamide (20 ml) and the suspension is stirred at 85° C. for 2.5 h. After cooling to room temperature the reaction solution is poured into water (300 ml), neutralized with concentrated acetic acid and extracted with chloroform (5×50 ml). The combined organic extracts are washed again with water (100 ml) and concentrated under high vacuum at low temperature. The substance is prepurified by column chromatography (silica gel 60, 0.040–0.063 mm, Merck No. 9385; inactivated by stirring with aqueous triethylamine/phosphate buffer pH 3 and subsequent sucking dry) (mobile phase: dichloromethane/isopropanol/-acetonitrile 80/12/8). Final purification is carried out by medium pressure chromatography (silica gel Macherey & Nagel Nucleosil 100–1525; inactivated by stirring with aqueous triethylamine/phosphate buffer pH 3 and subsequent sucking dry) (mobile phase: dichloromethane/isopropanol/acetonitrile 80/12/8). Yield: 150 mg (11%); purity>98%.

Physical data:

Rf: 0.30 (mobile phase: dichloromethane/isopropanol/acetonitrile 80/12/8). Melting point: 120° C. (decomposes). $[\alpha]^D{}_{20}$=+335° (c=0.02 in $CHCl_3$). $^1$H-NMR (200 MHz in $CDCl_3$): δ13.61 (s, 1H, OH-11), 12.83 (s, 1H, OH-6), 12.15 (s, 1H, OH-4), 7.88 (dd, 1H, $J_{1, 2}$=7.5 HZ, $J_{1, 3}$=1.1 HZ, H-1), 7.72 (t, 1H, $J_{1,2}=J_{2,3}=7.5$ HZ, H-2), 7.32 (dd, 1H, $J_{1,3}=1.1$ Hz, $J_{2,3}=7.5$ Hz, H-3), 5.52 (bs, 1H, H-1'), 5.30 (dd, 1H, $J_{7,8a}=1.4$ Hz, $J_{7,8b}=4.1$ HZ, H-7), 4.90 (s, 1H, H-10), 4.09 (q, 1H, $J_{5',6'}=6.5$ Hz, H-5'), 4.02 (s, 1H, OH), 3.72 (bs, 1H, H-4), 2.99 (m, 1H, H-2"), 2.79 (dd, 1H, $J_{1a'',1b''}=-11.6$ HZ, $J_{1a'',2''}=3.4$ HZ, H-1a"), 2.75 (t, $J_{3a'',3b''}=J_{2'',3a''}=4.3$ HZ, 1H, H-3a"), 2.55 (m, 1H, H-3'), 2.45 (dd, 1H, $J_{2'',3b''}=2.7$ Hz, $J_{3a'',3b''}=4.9$ HZ, H-3b"), 2.37 (dd, 1H, $J_{1a'',1b''}=-11.6$ HZ, $J_{1b'',2''}=3.1$ HZ, H-1b"), 2.36 (s, 3H, NCH$_3$), 2.25 (dd, 1H, $J_{7,8a}=1.4$ HZ, $J_{8a,8b}=-11.0$ HZ, H-8a), 2.15 (dd, 1H, $J_{7,8b}=4.1$ HZ, $J_{8a,8b}=-11.1$ HZ, H-8b), 1.82 (m, 4H, H-13a, H-13b, H-2a', H-2e'), 1.41 (d, 3H, $J_{5',6'}=6.5$ Hz, H-6'), 1.12 (t, 3H, $J_{13,14}=7.5$ HZ, H-14) ppm.
$^{13}$C-NMR (50 MHz in CDCl$_3$): $\delta$190.6 (C-5), 186.1 (C-12), 162.6 (C-4), 157.2 (C-11), 156.7 (C-6), 138.6 (C-10a), 137.1 (C-2), 134.9 (C-6a), 133.2 (C-12a), 124.9 (C-3), 119.7 (C-1), 115.9 (C-4a), 112.0 (C-5a), 111.4 (C-11a), 101.3 (C-1'), 71.8 (c-9), 70.8 (C-7), 66.7 (C-5'), 66.5 (C-10), 66.3 (C-4'), 57.9 (C-3'), 54.9 (C-1"), 50.3 (C-2"), 45.3 (C-3"), 39.1 (C-NCH$_3$), 32.8 (C-8), 30.3 (C-13), 28.5 (C-2'), 17.0 (C-6'), 6.6 (C-14) ppm. Mass spectrum: FAB-MS m/z 586 (M$^+$). UV spectrum: $\lambda_{max}^{MeOH}$nm ($\epsilon$) 230 (25,200), 292 (10,000), 494 (17,200), 528 (13,500), 587 (4,400). IR spectrum: (KBr)cm$^{-1}$ 3440 ($v_{max}$), 2964, 1600, 1460, 1437, 1405, 1291, 1237, 1198, 1165, 1130, 1067, 1022, 983.

The configuration at the glycidyl radical was determined as follows: The epoxide of the compound from Example 1 was opened in aqueous acid medium as described in the literature (for example Parker et al. Chem. Rev. 5.9, 737 (1959)) so that cleavage takes place at the most substituted C-O bond and the diol 5 is obtained via transition state 3. Under the basic reaction conditions for preparing the compound from Example 1, small amounts of the by-product 4, which is produced by basic epoxide opening with cleavage of the least substituted C-O bond as described in the literature (for example Parker et al. Chem. Rev. 59,737 (1959)), is obtained. This cyclic carbonate can be converted into the diol 6 by treatment with sodium methanolate. The diols 5 and 6 were prepared by a different route as described in the Patent DE 3,641,833 A1 from optically pure glyceraldehyde and compared with the products obtained from the epoxide opening by means of HPLC analysis. It has to be concluded from the formation of products 5 and 6 that the product from Example 1 has the R configuration at the glycidyl radical.

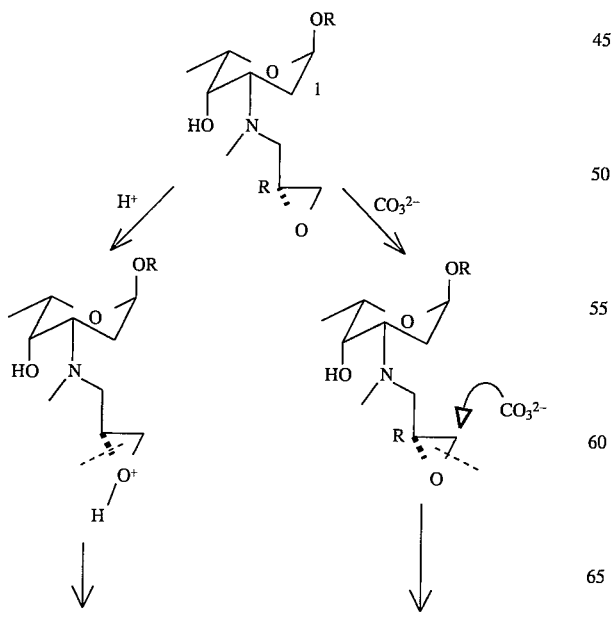

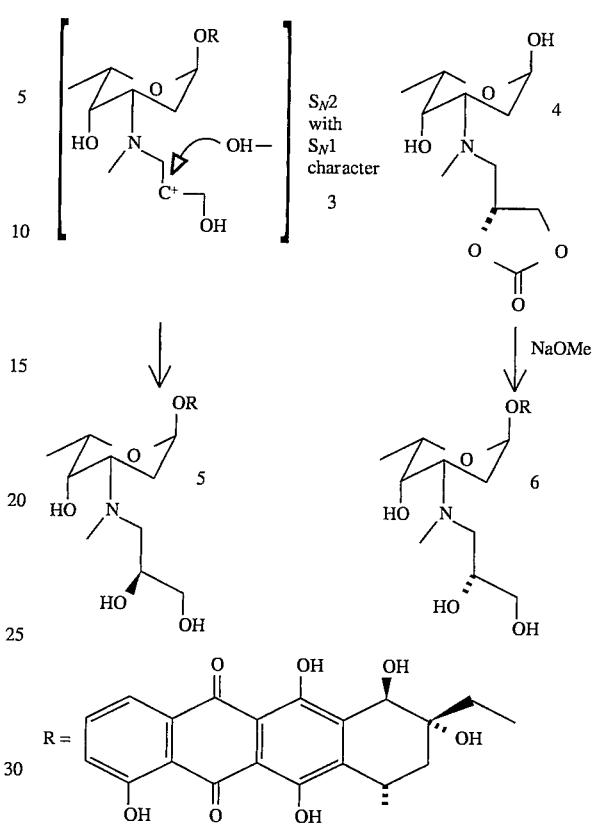

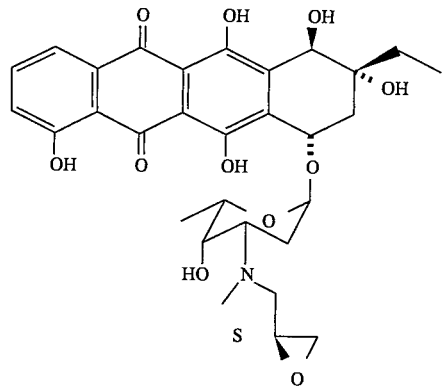

R =

Example 2:
7-O-(3-N-Methyl-3-N-(S)-glycidyl-$\alpha$-L-daunosaminyl)-$\beta$-rhodomycine 7-O-(3-N-Methyl-$\alpha$-L-daunosaminyl)-$\beta$-rhodomycinone was reacted with (S)-glycidyl tosylate, worked up and purified in accordance with Example 1.

Physical data: Rf: 0.35 (mobile phase: dichloromethane/isopropanol/acetonitrile 80/12/8). Melting point: 212°–215° C. $[\alpha]^D_{20}=+187°$ (c=0.075 in CHCl$_3$). $^1$H-NMR (400 MHz in CDCl$_3$): $\delta$13.58 (s, 1H, OH-11), 12.81 (s, 1H, OH-6), 12.11 (s, 1H, OH-4), 7.87 (dd, 1H, $J_{1,2}=7.5$ Hz, $J_{1,3}=1.1$ Hz, H-1), 7.71 (t, 1H, $J_{1,2}=J_{2,3}=J_{2,3}=7.5$ Hz, H-2), 7.31 (dd, 1H, $J_{1,3}=1.1$ Hz, $J_{2,3}=7.5$ Hz, H-3), 5.51 (bs, 1H, H-1'), 5.14 (dd, 1H, $J_{7,8a}=1.8$ Hz, $J_{7,8b}=4.0$ Hz, H-7), 4.90 (s, 1H, H-10), 4.08 (q, 1H, $J_{5',6'}=6.6$ Hz, H-5'), 4.03 (s, 1H, OH), 3.69 (bs, 1H, H-4), 2.99 (m, 1H, H-2"), 2.95 (dd, 1H, $J_{1a'',1b''}=-14.4$ HZ, $J_{1a'',2''}=2.8$ HZ, H-1a"), 2.72 (dd, $J_{3a'',3b''}=-4.8$ HZ, $J_{2'',3a''}=4.1$ HZ, 1H, H-3a"), 2.54 (m, 1H, H-3'), 2.49 (dd, 1H, $J_{2'',3b''}$=2.3 Hz, $J_{3a'',3b''}$=4.8 HZ, H-3b"), 2.32 (dd, 1H, $J_{1a'',1b''}$=–14.4 HZ, $J_{1b'',2''}$=5.7 HZ, H-1b"), 2.31 (s, 3H, NCH$_3$), 2.24 (dd, 1H, $J_{7,8a}$=1.8 HZ, $J_{8a,8b}$=–14.0 HZ, H-8a), 2.11 (dd, 1H, $J_{7,8b}$=4.0 Hz, $J_{8a,8b}$=–14.0 Hz, H-8b), 1.82 (m, 4H, H-13a, H-13b, H-2a', H-2e'), 1.41 (d 3H) $J_{5',6'}$=6.6 Hz, H-6'), 1.12 (t, 3H, $J_{13,14}$=7.5 HZ, H-14) ppm.

$^{13}$C-NMR (100 MHz in CDCl$_3$): δ190.5 (C-5), 186.0 (C-12), 162.5 (C-4), 157.0 (C-11), 156.6 (C-6), 138.4 (C-10a), 136.9 (C-2), 134.7 (C-6a), 133.0 (C-12a), 124.8 (C-3), 119.5 (C-1), 115.7 (C-4a), 111.9 (C-5a), 111.2 (C-11a), 101.1 (C-1'), 71.7 (C-9), 70.6 (C-7), 66.5 (C-5'), 66.4 (C-10), 66.0 (C-4'), 57.6 (C-3'), 54.4 (C-1"), 50.4 (C-2"), 44.5 (C-3"), 39.1 (C-NCH$_3$), 32.6 (C-8), 30.2 (C-13), 28.4 (C-2'), 16.8 (C-6'), 6.4 (C-14) ppm.

Mass spectrum: FAB-MS m/z 586 (M$^+$). UV spectrum: $\lambda_{max}^{MeOH}$nm (ε) 235 (62,800), 295 (13,900), 512 (18,500), 541 (21,700), 586 (17,400). IR spectrum: (KBr)cm$^{-1}$ 3446 ($v_{max}$), 2928, 1602, 1460, 1437, 1404, 1290, 1236, 1198, 1166, 1130, 1067, 1024, 982.

We claim:

1. An N-glycidylanthracycline derivative of the following formula I,

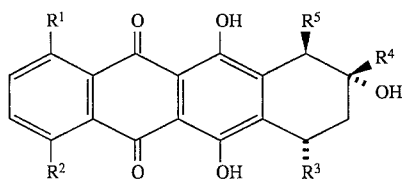

in which

R$^1$ is hydrogen or a hydroxyl group,

R$^2$ is hydrogen, a hydroxyl group or an alkyloxy (C$_1$–C$_4$) group,

R$^3$ is hydrogen, a hydroxyl group or a structure of the formula II

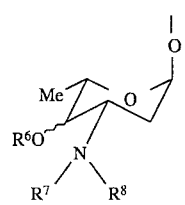

R$^4$ is CH$_2$CH$_3$, COCH$_3$, COCH$_2$OH, CHOHCH$_3$ or CHOHCH$_2$OH,

R$^5$ is hydrogen, a hydroxyl group, a methoxycarbonyl group or a structure of the formula II, R$^6$ is hydrogen, an alkyl group (C$_1$–C$_4$), an allyl group, a benzyl group or mono- or di-methyloxy-substituted benzyl group or a tetrahydropyranyl group, R$^7$ is hydrogen, an alkyl group (C$_1$–C$_4$), an allyl group, a benzyl group or a mono- or di-methyloxy-substituted benzyl group, and R$^8$ is a structure of the formula III or IV

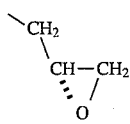

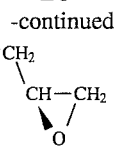

or the salts thereof with an inorganic or organic acid; and in which either one or both of R$^3$ and R$^5$ is a structure of the formula II.

2. N-glycidylanthracycline derivative as claimed in claim 1 in which

R$^1$ is hydrogen or a hydroxyl group,

R$^2$ is hydrogen, a hydroxyl group or a methoxy group,

R$^3$ is a structure of the formula II,

R$^4$ is CH$_2$CH$_3$, COCH$_2$OH, CHOHCH$_3$ or CHOHCH$_2$OH,

R$^5$ is hydrogen, a hydroxyl group, a methoxycarbonyl group or a structure of the formula II, R$^6$ is hydrogen, an alkyl group (C$_1$–C$_4$), an allyl group, a benzyl group or mono- or di-methyloxy-substituted benzyl group or a tetrahydropyranyl group, R$^7$ is hydrogen, an alkyl group (C$_1$–C$_4$), an allyl group, a benzyl group or mono- or di-methyloxy-substituted benzyl group and R$^8$ is a structure of the formula III or IV.

3. N-glycidylanthracycline derivative as claimed in claim 1, in which

R$^1$ is hydrogen or a hydroxyl group,

R$^2$ is hydrogen, a hydroxyl group or a methoxy group,

R$^3$ is a structure of the formula II,

R$^4$ is CH$_2$CH$_3$, COCH$_3$, COCH$_2$OH, CHOHCH$_3$ or CHOHCH$_2$OH,

R$^5$ is hydrogen, a hydroxyl group or a methoxy-carbonyl group,

R$^6$ is hydrogen, an alkyl group (C$_1$–C$_4$), an allyl group, a benzyl group or mono- or di-methyloxy-substituted benzyl group or a tetrahydropyranyl group, R$^7$ is hydrogen, an alkyl group (C$_1$–C$_4$), an allyl group, a benzyl group or mono- or di-methyloxy-substituted benzyl group and R$^8$ is a structure of the formula III or IV.

4. N-glycidylanthracycline derivative as claimed in claim 1, in which

R$^1$ is hydrogen,

R$^2$ is hydrogen, a hydroxyl group or a methoxy group,

R$^3$ is a structure of the formula II,

R$^4$ is CH$_2$CH$_3$, COCH$_3$, COCH$_2$OH, CHOHCH$_3$ or CHOHCH$_2$OH,

R$^5$ is hydrogen, a hydroxyl group or a methoxy-carboyl group,

R$^6$ is hydrogen or a tetrahydropyranyl group,

R$^7$ is hydrogen, an alkyl group (C$_1$–C$_4$), an allyl group, a benzyl group or mono- or di-methyloxy-substituted benzyl group and R$^8$ is a structure of the formula III or IV.

5. N-glycidylanthracycline derivative as claimed in claim 1, in which

R$^1$ is hydrogen,

R$^2$ is hydrogen, a hydroxyl group or a methoxy group,

R$^3$ is a structure of the formula II,

R$^4$ is CH$_2$CH$_3$, COCH$_2$OH, CHOHCH$_3$ or CHOHCH$_2$OH, $R^5$ is hydrogen, a hydroxyl group or a methoxy-carbonyl group,
$R^6$ is hydrogen or a tetrahydropyranyl group,
$R^7$ is hydrogen, an alkyl group ($C_1$–$C_4$), an allyl group and
$R^8$ is a structure of the formula III or IV.

6. N-glycidylanthracycline derivative as claimed in claim 1, in which
$R^1$ is hydrogen,
$R^2$ is a hydroxyl group or a methoxy group,
$R^3$ is a structure of the formula II,
$R^4$ is $CH_2CH_3$, $COCH_3$ or $COCH_2OH$,
$R^5$ is hydrogen or a hydroxyl group,
$R^6$ is hydrogen,
$R^7$ is hydrogen, an alkyl group ($C_1$–$C_4$) or an allyl group and
$R^8$ is a structure of the formula III or IV.

7. N-glycidylanthracycline derivative as claimed in claim 1, in which
$R^1$ is hydrogen,
$R^2$ is a hydroxyl group,
$R^3$ is a structure of the formula II,
$R^4$ is $CH_2CH_3$,
$R^5$ is a hydroxyl group,
$R^6$ is hydrogen,
$R^7$ is a methyl group and
$R^8$ is a structure of the formula III or IV.

8. N-glycidylanthracycline derivative as claimed in claim 1, in which
$R^1$ is hydrogen,
$R^2$ is a hydroxyl group,
$R^3$ is a structure of the formula II,
$R^4$ is $CH_2CH_3$,
$R^5$ is a hydroxyl group,
$R^6$ is hydrogen,
$R^7$ is a methyl group and
$R^8$ is a structure of the formula III.

9. A pharmaceutical composition comprising a compound as claimed in claim 1 together with a pharmaceutically acceptable carrier.

* * * * *

UNITED STATES PATENT AND TRADEMARK OFFICE
CERTIFICATE OF CORRECTION

PATENT NO. : 5,602,108
DATED : February 11, 1997
INVENTOR(S) : Manfred GERKEN et al.

It is certified that error appears in the above-indentified patent and that said Letters Patent is hereby corrected as shown below:

Claim 2, column 10, line 15, after "$CH_2CH_3$," insert --$COCH_3$,--.

Signed and Sealed this

Fifth Day of August, 1997

Attest:

BRUCE LEHMAN

Attesting Officer     Commissioner of Patents and Trademarks